(12) United States Patent
Sato et al.

(10) Patent No.: US 7,504,239 B2
(45) Date of Patent: Mar. 17, 2009

(54) METHOD OF DIFFERENTIATING BEER YEAST

(75) Inventors: Masahide Sato, Yaizu (JP); Youichi Tsuchiya, Yaizu (JP)

(73) Assignee: Sapporo Breweries Limited, Tokyo (JP)

( * ) Notice: Subject to any disclaimer, the term of this patent is extended or adjusted under 35 U.S.C. 154(b) by 721 days.

(21) Appl. No.: 10/067,241

(22) Filed: Feb. 7, 2002

(65) Prior Publication Data

US 2003/0104405 A1 Jun. 5, 2003

(30) Foreign Application Priority Data

Feb. 9, 2001 (JP) .............................. 2001-034113

(51) Int. Cl.
*C12P 19/34* (2006.01)
*C12Q 1/68* (2006.01)
*C07H 21/04* (2006.01)
*C07H 21/00* (2006.01)

(52) U.S. Cl. .................... 435/91.2; 435/6; 536/23.7; 536/24.33; 536/25.3

(58) Field of Classification Search ............... 435/6, 435/69.9, 91.1; 536/23.1, 24.1
See application file for complete search history.

(56) References Cited

U.S. PATENT DOCUMENTS

| | | | | |
|---|---|---|---|---|
| 5,200,313 | A * | 4/1993 | Carrico ........................ | 435/6 |
| 5,866,374 | A * | 2/1999 | Kobayashi et al. ......... | 435/69.9 |
| 2002/0119455 | A1* | 8/2002 | Chan ........................... | 435/6 |
| 2006/0210967 | A1* | 9/2006 | Agan et al. .................. | 435/5 |
| 2006/0223122 | A1* | 10/2006 | Fogo et al. .................. | 435/7.2 |
| 2006/0223197 | A1* | 10/2006 | Vielsack ..................... | 436/524 |
| 2006/0234234 | A1* | 10/2006 | Van Dongen et al. ......... | 435/6 |
| 2006/0246453 | A1* | 11/2006 | Kato et al. ................... | 435/6 |
| 2006/0286570 | A1* | 12/2006 | Rowlen et al. .............. | 435/6 |
| 2007/0009954 | A1* | 1/2007 | Wang et al. .................. | 435/6 |
| 2007/0031829 | A1* | 2/2007 | Yasuno et al. ............... | 435/6 |
| 2007/0042400 | A1* | 2/2007 | Choi et al. ................... | 435/6 |

FOREIGN PATENT DOCUMENTS

| | | |
|---|---|---|
| EP | 0 759 465 | 2/1997 |
| JP | 8-266287 | 10/1996 |
| JP | 9-224676 | 9/1997 |
| JP | 11-56366 | 3/1999 |
| JP | 2001-8684 | 1/2001 |

OTHER PUBLICATIONS

Zhang et a., Bioinformatics, vol. 19, No. 1, 2003, pp. 14-21.*
New England BioLabs Catalog, 2000, p. 125.*
O. Kobayashi, et al., Journal of Bacteriology, vol. 180, No. 24, pp. 6503-6510, "Region of FL01 Proteins Responsible for Sugar Recognition", Dec. 1998.
M. Sato, et al., J. Am. Soc. Brew. Chem., vol. 59, No. 3, pp. 130-134, "Genetic Instability in Flocculation of Bottom-Fermenting Yeast", 2001.
M. Jibiki, et al., J. Am. Soc. Brew. Chem., vol. 59, No. 3, pp. 107-110, "Application of Polymerase Chain Reaction to Determine the Flocculation Properties of Brewer's Lager Yeast", 2001.
J. Watari, et al., Yeast, vol. 10, pp. 211-225, "Molecular Cloning and Analysis of the Yeast Flocculation Gene FL01", 1994.
H. Yamagishi, et al., Journal of Applied Microbiology, vol. 86, No. 3, pp. 505-513, XP-002264705, "Differentiation Between Brewing and Non-Brewing Yeasts Using a Combination of PCR and RFLP", Mar. 1999.
M. Sato, et al., Journal of Bioscience and Bioengineering, vol. 93, No. 4, pp. 395-398, XP-001156816, "Analysis of an Inactivated Lg-FLO1 Gene Present in Bottom-Fermenting Yeast", 2002.

* cited by examiner

*Primary Examiner*—Bradley L Sisson
(74) *Attorney, Agent, or Firm*—Oblon, Spivak, McClelland, Maier & Neustadt, P.C.

(57) ABSTRACT

The method of differentiating beer yeast of the invention is a method which comprises a first step of synthesizing a primer capable of amplifying the linker portion between a base sequence (A) and a base sequence (B) in a novel gene (C) which has the base sequence (B) comprising a portion of yeast chromosome IX linked downstream from the base sequence (A) comprising a portion of the N-terminal end of yeast gene Lg-FLO1, and which includes the base sequences listed as SEQ. ID. Nos. 1-6 of the Sequence Listing; a second step of carrying out a PCR (Polymerase Chain Reaction) using the primer synthesized in the first step and DNA separated from a yeast specimen; and a third step of differentiating whether the yeast is bottom-fermenting yeast or wild yeast, based on the PCR amplification product obtained from the second step.

6 Claims, 5 Drawing Sheets

1: λ/Hind III
2: HindIII cleavage fragment amplified from flocculent strain
3: Fragment amplified by inverse PCR from non-flocculent strain

METHOD OF DIFFERENTIATING BEER YEAST

BACKGROUND OF THE INVENTION

1. Field of the Invention

The present invention relates to a method of differentiating bottom-fermenting yeast (bottom-fermenting yeast for brewering) and wild yeast.

2. Related Background Art

In the process of brewing of alcoholic malt beverages (beer, low-malt beer and the like), inclusion of wild yeast not used for brewing, such as *Hansenula*, *Brettanomyces* and *Candida*, or *Saccharomyces* strains not used as brewing yeasts, results in inferior aroma characteristics of the alcoholic malt beverages, and in some cases causes clouding or off-flavor.

It is therefore important, from the standpoint of maintaining and controlling the yeast fermentation properties and the aroma characteristics of alcoholic malt beverages, to rapidly differentiate whether or not yeast detected in the process of brewing of alcoholic malt beverages is bottom-fermenting yeast.

Identification of yeast has in the past been accomplished by traditional physiological, biochemical and morphological methods, but most of these have lacked speed and accuracy. Bottom-fermenting yeast is often classified as belonging to the genus *Saccharomyces* (presently classified as *Saccharomyces pastorianus*), and it has been difficult to differentiate this bottom-fermenting yeast from other *Saccharomyces* yeast strains which are not bottom-fermenting yeast, such as *Saccharomyces cerevisiae*, *Saccharomyces bayanus* and *Saccharomyces diastaticus*, using the existing traditional methods.

In order to solve this problem, Japanese Patent Application Laid-Open Gazette No. HEI. 11-56366 discloses a method of differentiating brewer's yeast from non-brewer's yeast by using the PCR method for detection of sequence repeats of the FLO1 gene of *Saccharomyces*. However, it has been reported that the repeating sequences of the FLO1 gene and Lg-FLO1 gene are extremely unstable (Yeast, 10:211-225, 1994, J. Bacteriol. 180(24):6503-6510, 1998), and in some cases the sequence repeats are completely dropped. The method described in Japanese Patent Application Laid-Open Gazette No. HEI. 11-56366 has therefore been associated with the problem whereby even bottom-fermenting yeast is mistakenly identified as wild yeast.

SUMMARY OF THE INVENTION

It is an object of the present invention, which has been accomplished in light of the problems of the prior art, to provide a method of differentiating between bottom-fermenting yeast and wild yeast with a high degree of accuracy.

As a result of much diligent research directed toward achieving this object, the present inventors have completed the present invention upon finding that it is possible to differentiate between bottom-fermenting yeast and wild yeast with a high degree of accuracy by using a primer set capable of amplifying the linker portion between a base sequence (A) and a base sequence (B) in a novel yeast gene (C) which includes base sequence (A) comprising a portion of the N-terminal end of gene Lg-FLO1 and base sequence (B) comprising yeast gene YIL169c.

The method of differentiating beer yeast according to the invention is a method which comprises a first step of synthesizing a primer capable of amplifying the linker portion between a base sequence (A) and a base sequence (B) in a novel gene (C) which has the base sequence (B) comprising a portion of yeast chromosome IX linked downstream from the base sequence (A) comprising a portion of the N-terminal end of yeast gene Lg-FLO1, and which includes the base sequences listed as SEQ. ID. Nos. 1-6 of the Sequence Listing; a second step of carrying out a PCR (Polymerase Chain Reaction) using the primer synthesized in the first step and DNA separated from a yeast specimen; and a third step of differentiating whether the yeast is bottom-fermenting yeast or wild yeast, based on the PCR amplification product obtained from the second step.

The primer used here is preferably a pair of primers including respectively the base sequences listed as SEQ. ID. No.7 and No.8 of the Sequence Listing.

The base sequences of the primers may have one or more base substitutions, deletions or insertions, and the primers preferably function as primers for PCR.

The method of differentiating beer yeast according to the invention is also a method which comprises a first step of synthesizing a primer capable of amplifying a portion of a base sequence (A) in a novel gene (C) which has a base sequence (B) comprising a portion of yeast chromosome IX linked downstream from the base sequence (A) comprising a portion of the N-terminal end of yeast gene Lg-FLO1, and which includes the base sequences listed as SEQ. ID. Nos. 1-6 of the Sequence Listing; a second step of carrying out a PCR (Polymerase Chain Reaction) using the primer synthesized in the first step and DNA separated from a yeast specimen; and a third step of differentiating whether the yeast is bottom-fermenting yeast or wild yeast, based on the PCR amplification product obtained from the second step.

The primer used here is preferably a pair of primers including respectively the base sequences listed as SEQ. ID. No.9 and No.10 of the Sequence Listing.

The base sequences of these primers may also have one or more base substitutions, deletions or insertions, and the primers preferably function as primers for PCR.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
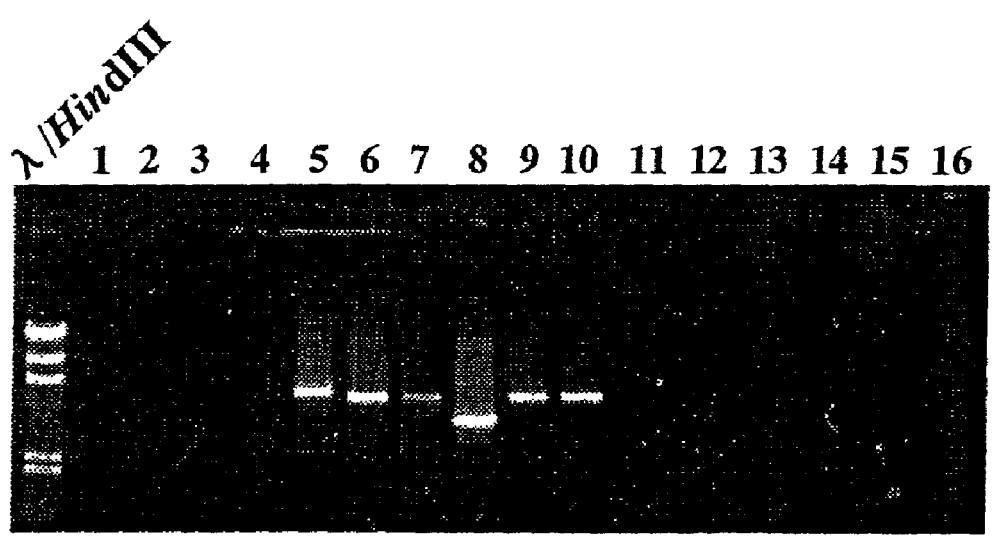
FIG. 1 is an electrophoresis photograph for differentiation between bottom-fermenting yeast and wild yeast using primers having the base sequences listed as SEQ. ID. Nos. 10 and 11.

Preferred embodiments of the invention will now be explained in detail.

The following explanation concerns a first embodiment of the invention.

The method of differentiating beer yeast according to the first embodiment of the invention is a method which comprises a first step of synthesizing a primer capable of amplifying the linker portion between a base sequence (A) and a base sequence (B) in a novel gene (C) which has the base sequence (B) comprising a portion of yeast chromosome IX linked downstream from the base sequence (A) comprising a portion of the N-terminal end of yeast gene Lg-FLO1, and which includes the base sequences listed as SEQ. ID. Nos. 1-6 of the Sequence Listing; a second step of carrying out a PCR (Polymerase Chain Reaction) using the primer synthesized in the first step and DNA separated from a yeast specimen; and a third step of differentiating whether the yeast is bottom-fermenting yeast or wild yeast, based on the PCR amplification product obtained from the second step.

The first step according to the first embodiment of the invention will now be explained.

The first step according to the invention is a step of synthesizing a primer set capable of amplifying the linker portion between a base sequence (A) and a base sequence (B) in a novel gene (C) which has the base sequence (B) comprising a portion of yeast chromosome IX linked downstream from the base sequence (A) comprising a portion of the N-terminal end of yeast gene Lg-FLO1, and which includes the base sequences listed as SEQ. ID. Nos. 1-6 of the Sequence Listing.

Base sequence (A) according to the invention comprises a portion of the N-terminal end of yeast gene Lg-FLO1. Yeast gene Lg-FLO1 has been reported as a gene coding for protein Lg-FLO1 having the function of imparting a flocculating property to yeast (Japanese Patent Application Laid-Open Gazette No. HEI. 8-266287).

The N-terminal portion of the Lg-FLO1 gene has been reported as a region which contributes the property whereby yeast flocculation is inhibited by sugars such as maltose and glucose (J. Bacteriol. 180(24):6503-6510, 1998).

Flocculation is the property whereby yeast dispersed during the process of fermentation aggregate and adhere and bind to each other at the cell surfaces, forming flock. Some strains of bottom-fermenting yeast have a property whereby the cells flocculate in the fermentation solution and precipitate, allowing them to be easily and rapidly separated from the solution, while other strains have a property whereby they tend not to flocculate, resulting in their dispersion and suspension for relatively long periods. The former are referred to as "flocculent strain (flocculent yeast)" while the latter are referred to as "non-flocculent strain (non-flocculent yeast)".

Base sequence (B) according to the invention will now be explained.

Base sequence (B) according to the invention is a base sequence comprising a portion of yeast chromosome IX, and it includes the base sequence of yeast gene YIL169c. Yeast gene YIL169c has high base sequence homology with the glucan 1,4-alpha-glucosidase gene, but its detailed function is still unknown.

The novel gene of the invention includes these base sequences (A) and (B), and also includes the base sequences listed as SEQ. ID. Nos. 1-6 of the Sequence Listing. The base sequences listed as SEQ. ID. Nos. 1-6 of the Sequence Listing correspond to 21340-21818 bp (SEQ. ID. No.1), 21743-22190 bp (SEQ. ID. No.2), 22353-22865 bp (SEQ. ID. No.3), 22926-23398 bp (SEQ. ID. No.4), 23944-24219 bp (SEQ. ID. No.5) and 24408-24997 bp (SEQ. ID. No.6), respectively, from the left telomere end of chromosome IX of *Saccharomyces cerevisiae*. Each of these sequences differs in about 1-20 bases when compared with the base sequence of chromosome IX of *Saccharomyces cerevisiae* found in the data base, but the differences are believed to be due to genetic polymorphisms between the yeast strains or errors in determining the base sequences, and the genes are substantially identical. Consequently, the novel gene (C) according to the invention not only includes the exact base sequences listed as SEQ. ID. Nos. 1-6 of the Sequence Listing but also base sequences that differ from the sequences listed as SEQ. ID. Nos. 1-6 of the Sequence Listing within a range in which they may still be considered substantially the same gene. Specifically, genes differing in 1-20 bases for each base sequence among the base sequences including SEQ. ID. Nos. 1-6 maybe considered substantially identical to genes which include SEQ. ID. Nos. 1-6.

Figure 5:
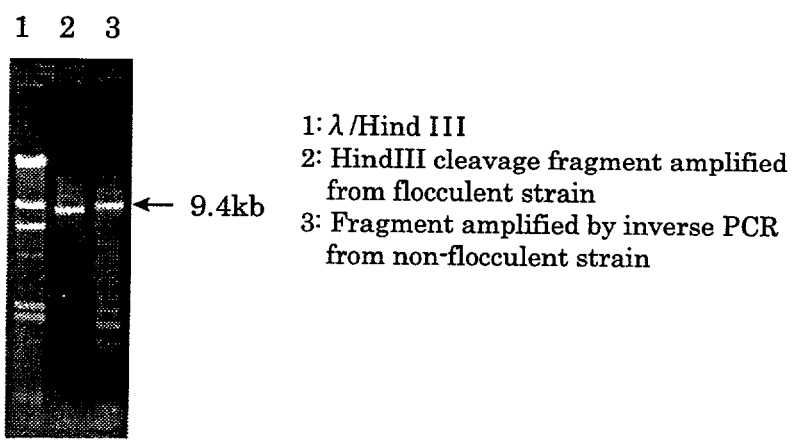
FIG. 5 is an electrophoresis photograph of the Lg-FLO1 analogue gene obtained by inverse PCR.

Thus, the novel gene of the invention is a gene having a total length of 9.4 kbp as seen in FIG. 5, and having a structure wherein a base sequence comprising a portion of *Saccharomyces cerevisiae* chromosome IX is linked downstream from base sequence (A) comprising a portion of the yeast gene Lg-FLO1. It is the belief of the present inventors that the bottom-fermenting yeast according to the invention undergoes genomic DNA recombination when the strain is established, resulting in linkage between a portion of the Lg-FLO1 gene and a portion of chromosome IX to produce a gene having the base sequence of the novel gene (C).

Since the aforementioned novel gene has a structure wherein base sequence (B) comprising a portion of *Saccharomyces cerevisiae* chromosome IX is linked downstream from base sequence (A) comprising a portion of gene Lg-FLO1, as explained above, the "linker portion between a base sequence (A) and a base sequence (B)" in the novel gene is the linker portion between base sequence (A) and base sequence (B) produced as the result.

The primer set of the invention is selected at locations which allow this linkage site to be amplified by PCR. That is, one of the primers of the primer set is selected in the sense direction on base sequence (A) of the novel gene (C) while the other primer of the primer set is selected in the antisense direction on base sequence (B) of the novel gene.

The number of bases of each of the primers is not particularly restricted, but is preferably 10-50 bp and more preferably 15-30 bp. The sequence of each is also not particularly restricted, but preferably the primer in the sense direction on the Lg-FLO1 gene is 5'-GGAATACTGCCTCTTGGAGT-3' (SEQ. ID. No.7) and the primer in the antisense direction on chromosome IX is 5'-GGATTCTTCAGCGTTGAAGT-3' (SEQ. ID. No.8).

The primer set according to the invention is preferably a primer set composed of primers having base sequences including the base sequences of the primers of SEQ. ID. Nos. 7 and 8. Specifically, the primers may also include, for example, restriction enzyme recognition sequences in consideration of subsequent cloning of the amplification product.

So long as the primers have the function as primers for PCR, the primer set may consist of primers with one or more substitutions, deletions or insertions. Here, "function as primers for PCR" means that they are capable of functioning as primers for PCR using the aforementioned novel gene (C) as the template. That is, there are no particular restrictions on the base sequences so long as the primers are able to anneal to the novel gene under ordinary PCR conditions.

In the first step according to the invention, such primers may be synthesized with a DNA synthesizer or the like.

The second step according to the first embodiment of the invention will now be explained.

The second step according to the invention is a step of carrying out a PCR (Polymerase Chain Reaction) using the primer set synthesized in the first step and DNA separated from a yeast specimen.

There are no particular restrictions on the method of extracting the DNA from the yeast specimen, and any publicly known method may be used for extraction. Specifically, cultured yeast cells may be collected by centrifugal separation and the DNA extracted from the yeast by following the procedure of Holm et al. (Gene, 42:169-173, 1986).

In the second step of the invention, the extracted DNA is used as the template for PCR using the primers synthesized in the first step. The PCR may be carried out according to a publicly known protocol, and for example, the protocol described in FEMS Microbiol. Lett., Vol. 108, p. 259-264 (1993) may be followed. The PCR conditions may be appropriately set according to the Tm (melting temperature) of the primers used, but the conditions are preferably a denaturation temperature of 90-98° C., an annealing temperature of 40-75° C. and an extension temperature of 65-75° C., with 10 or more cycles. Preferably, the denaturation temperature is maintained for 10 seconds to 2 minutes, the annealing temperature is maintained for 20 seconds to 2 minutes and the extension temperature is maintained for 1-20 minutes.

The third step according to the first embodiment of the invention will now be explained.

The third step according to the invention is a step of differentiating whether the yeast is bottom-fermenting yeast or wild yeast, based on the PCR amplification product obtained in the second step.

There are no particular restrictions on the method of differentiating whether the yeast is bottom-fermenting yeast or wild yeast based on the PCR product obtained in the second step, and for example, a portion of the PCR amplification product may be subjected to agarose gel electrophoresis and the presence or absence of the detected amplified fragments used to judge whether or not the yeast is bottom-fermenting yeast. Specifically, when a primer set having the nucleic acid sequences of SEQ. ID. Nos. 7 and 8, for example, is used for the PCR, an amplified band will be detected if the yeast specimen is bottom-fermenting yeast, but no band will be detected if the yeast is wild yeast.

Thus, the method according to the first embodiment of the invention allows detection of bottom-fermenting yeast irrespective of differences in bottom-fermenting yeast strains or the degree of flocculation of the bottom-fermenting yeast.

The following explanation concerns a second embodiment of the invention.

The method of differentiating beer yeast according to the second embodiment of the invention is a method which comprises a first step of synthesizing a primer capable of amplifying a portion of base sequence (A) in a novel gene (C) which has base sequence (B) comprising a portion of yeast chromosome IX linked downstream from base sequence (A) comprising a portion of the N-terminal end of yeast gene Lg-FLO1, and which includes the base sequences listed as SEQ. ID. Nos. 1-6 of the Sequence Listing; a second step of carrying out a PCR (Polymerase Chain Reaction) using the primer synthesized in the first step and DNA separated from a yeast specimen; and a third step of differentiating whether the yeast is bottom-fermenting yeast or wild yeast, based on the PCR amplification product obtained from the second step.

The first step according to the second embodiment of the invention will now be explained.

The first step is a step of synthesizing a primer set capable of amplifying a portion of base sequence (A) in a novel gene (C) which has base sequence (B) comprising a portion of yeast chromosome IX linked downstream from base sequence (A) comprising a portion of the N-terminal end of yeast gene Lg-FLO1, and which includes the base sequences listed as SEQ. ID. Nos. 1-6 of the Sequence Listing.

Here, the novel gene (C) is the same gene as the novel gene (C) according to the first embodiment of the invention.

In this step there is synthesized a primer set which is capable of amplifying a portion of base sequence (A) of the novel gene. While there are no particular restrictions on the number of bases of "a portion of base sequence (A)", it is preferably 50-20,000 bp and more preferably 100-10,000 bp.

The number of bases of each of the primers is not particularly restricted, but is preferably 10-50 bp and more preferably 15-30 bp. The sequence of each is also not particularly restricted, but preferably the primer in the sense direction is 5'-AACGTAGCATCAGGAAGTACACAAGCATGC-3' (SEQ. ID. No.9) and the primer in the antisense direction is 5'-GATCGGGTAATAGTAACCGGCGTACATGTA-3' (SEQ. ID. No.10).

The primer set according to the invention is preferably a primer set composed of primers having base sequences including the base sequences of the primers of SEQ. ID. Nos. 9 and 10. Specifically, the primers may contain, for example, restriction enzyme recognition sequences in consideration of subsequent cloning of the amplification product.

So long as the primers have the function as primers for PCR, the primer set may consist of primers with one or more substitutions, deletions or insertions. Here, "function as primers for PCR" means that they are capable of functioning as primers for PCR using the aforementioned novel gene (C) as the template. That is, there are no particular restrictions on the base sequences so long as the primers are able to anneal to the novel gene under ordinary PCR conditions.

In the first step according to the invention, such primers may be synthesized with a DNA synthesizer or the like.

The second step according to the second embodiment of the invention is a step of carrying out a PCR (Polymerase Chain Reaction) using the primers synthesized in the first step and DNA separated from a yeast specimen.

There are no particular restrictions on the method of extracting the DNA from the yeast specimen, and any publicly known method may be used for extraction. Specifically, cultured yeast cells may be collected by centrifugal separation and the DNA extracted from the yeast by following the procedure of Holm et al. (Gene, 42:169-173, 1986).

In the second step of the invention, the extracted DNA is used as the template for PCR using the primers synthesized in the first step. The PCR may be carried out according to a publicly known protocol, and for example, the protocol described in FEMS Microbiol. Lett., Vol. 108, p. 259-264 (1993) may be used. The PCR conditions may be appropriately set according to the Tm of the primers used, but the conditions are preferably a denaturation temperature of 90-98° C., an annealing temperature of 40-75° C. and an extension temperature of 65-75° C., with 10 or more cycles. Preferably, the denaturation temperature is maintained for 10 seconds to 2 minutes, the annealing temperature is maintained for 20 seconds to 2 minutes and the extension temperature is maintained for 1-20 minutes.

The third step according to the second embodiment of the invention will now be explained.

The third step according to the invention is a step of differentiating whether the yeast is bottom-fermenting yeast or wild yeast, based on the PCR amplification product obtained in the second step.

There are no particular restrictions on the method of differentiating whether the yeast is bottom-fermenting yeast or wild yeast based on the PCR product obtained in the second step, and for example, a portion of the PCR amplification product may be subjected to agarose gel electrophoresis and the presence or absence of the detected amplified fragments used to judge whether or not the yeast is bottom-fermenting yeast. Specifically, when a primer set having the nucleic acid sequences of SEQ. ID. Nos. 9 and 10, for example, is used for the PCR, an amplified band will be detected if the yeast specimen is bottom-fermenting yeast, but no band will be detected if the yeast is wild yeast.

Thus, the method according to the second embodiment of the invention allows detection of bottom-fermenting yeast irrespective of differences in bottom-fermenting yeast strains or the degree of flocculation of the bottom-fermenting yeast.

EXAMPLES

The present invention will now be explained in detail by way of examples and comparative examples, with the understanding that the invention is in no way limited by the examples.

Comparative Example 1

(Differentiation of Bottom-Fermenting Yeast Based on Lg-FLO1 Gene)

The following experiment was conducted for differentiation between bottom-fermenting yeast and wild yeast.

Extraction of the total DNA was accomplished by culturing 10 strains of bottom-fermenting yeast and 6 strains of wild yeast in 10 ml of YEPD medium (1% yeast extract, 2% bactopeptone, 2% glucose) each at 20° C. until the stationary phase, collecting the cells by centrifugal separation, and then following the procedure of Holm et al. (Gene, 42:169-173, 1986).

The PCR was carried out in the following manner. The two primers 5'-GGAATACTGCCTCTTGGAGT-3' (SEQ. ID. No.11) and 5'-TTACCATACGATTGCCAGCA-3' (SEQ. ID. No.12) were synthesized based on the Lg-FLO1 gene base sequence reported by Kobayashi et al. (J. Bacteriol. 180(24) 6503-6510, 1998). This set of primers was used for PCR using the total DNA of the yeasts shown in Table 1 as the templates. Nos. 1-16 in Table 1 correspond to the lane numbers in FIG. 1.

TABLE 1

| Name of strain (bottom-fermenting yeast) | Flocculating property evaluation | Name of strain (wild yeast) |
| --- | --- | --- |
| 1: NCYC965 | F0 | 11: *Saccharomyces cerevisiae* (ATCC 46967) |
| 2: NCYC1324 | F0 | |

TABLE 1-continued

| Name of strain (bottom-fermenting yeast) | Flocculating property evaluation | Name of strain (wild yeast) |
| --- | --- | --- |
| 3: W204 | F0 | 12: *Saccharomyces diastaticus* |
| 4: W71 | F1 | |
| 5: AJL3126 | F1 | 13: *Pichia* (IFO 0035) |
| 6: NCYC512 | F2 | 14: *Saccharomyces bayanus* (IFO 0676) |
| 7: NCYC719 | F2 | |
| 8: NCYC1250 | F2 | 15: *Candida albicans* (ATCC 10259) |
| 9: VLB202 | F2 | |
| 10: VLB He Bru | F2 | 16: *Saccharomyces uvarum* (ATCC 44968) |

The PCR conditions were 94° C. for 1 minute followed by 98° C. for 20 seconds and 68° C. for 3 minutes, repeated for 30 cycles. The total amount of template DNA added to the PCR reaction system was 0.5-1 μg for each, in consideration of reproducibility of the test. A portion of the reaction product was then subjected to electrophoresis in 1% agarose, and judgment of the yeast as bottom-fermenting yeast was based on the presence or absence of amplification, or the band size.

The degree of flocculation of each of the bottom-fermenting yeasts was evaluated in the following manner. A 0.6 g portion of the yeast collected by centrifugal separation after completion of fermentation was suspended in 20 ml of tap water. One milliliter of a 0.5 M acetate buffer solution (pH 4.5) containing 1500 ppm calcium ion was added to 9 ml of the yeast suspension, the mixture was manually shaken in a vertical manner and the degree of flocculation was visually judged on a 3-level scale. The scale was as follows: F0=No flocculation, F1=Weak flocculation, F2=Ordinary flocculation, F3=Strong flocculation.

As shown in FIG. 1, this method did not allow detection of some types of bottom-fermenting yeast, particularly strains with weak or no flocculation (F0 or F1), and therefore it could not be differentiated whether or not those strains were bottom-fermenting yeast.

Example 1

(Obtaining Novel Fused Gene Containing a Portion of Lg-FLO1 Gene N-Terminal End, and Partial Determination of Base Sequence)

Flocculating genes according to flocculent strains and non-flocculent strains of bottom-fermenting yeast were subjected to Northern and Southern analysis. Extraction and electrophoresis of the total RNA were carried out after culturing of flocculent and non-flocculent bottom-fermenting yeast in the same manner as Comparative Example 1, according to the method of Schmitt et al. (Nucleic Acids Research, 18(10): 3091, 1990). The RNA in the gel after electrophoresis was subjected to blotting using a Hybond-N+ (product of Amersham-Pharmacia Biotech, KK.), according to the included protocol.

For Southern analysis, total DNA extracted in the same manner as Comparative Example 1 was digested with restriction enzyme HindIII (Takara Shuzo Co., Ltd.) and then electrophoresed with 1% agarose gel and subjected to blotting with Hybond-N+ (product of Amersham-Pharmacia Biotech, KK.). Extraction of the RNA or DNA was accomplished using a DIG system (Roche).

The Lg-FLO1 and FLO1 partial DNA fragments used as probes were prepared in the following manner. The two primers 5'-AACGTAGCATCAGGAAGTACACAAGCATGC-3' (SEQ. ID. No.9) and 5'-GATCGGGTAATAGTAACCGGCGTACATGTA-3' (SEQ. ID. No.10) were synthesized based on the Lg-FLO1 N-terminal base sequence reported by Kobayashi et al. (J. Bacteriol. 180(24) 6503-6510, 1998). These primers were used for PCR using the total DNA of the flocculent bottom-fermenting yeasts as the templates. Separately, the two primers 5'-TTCCAACCAGTAGTTCCACC-3' (SEQ. ID. No.13) and 5'-GGTCGCGGAAGCCGTCT-GTG-3' (SEQ. ID. No.14) were synthesized based on the FLO1 C-terminal base sequence reported by Watari et al. (Yeast, 10:211-225, 1994). These primers were used for PCR in the same manner. The PCR conditions were the same as in Comparative Example 1.

The obtained DNA fragments were labeled according to the protocol for the DIG system (Roche) and subjected to Northern and Southern analysis.

Figure 2:
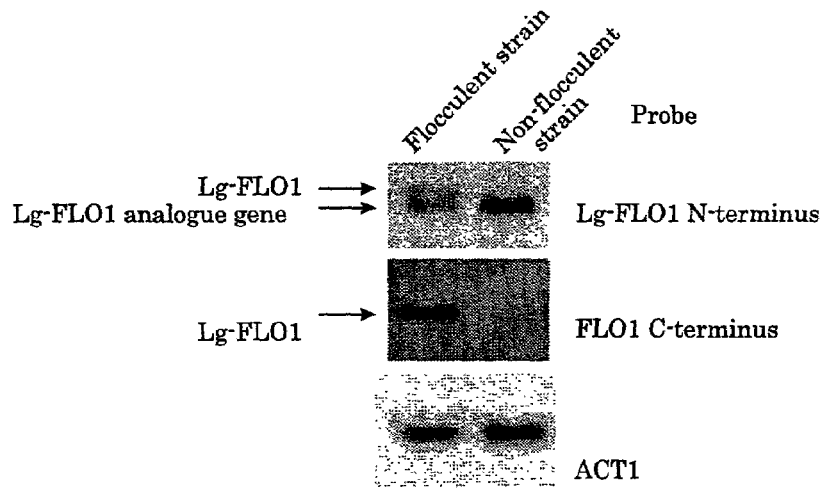
FIG. 2 is an autoradiogram showing the results of Northern analysis of the Lg-FLO1 analogue gene.
Figure 3:
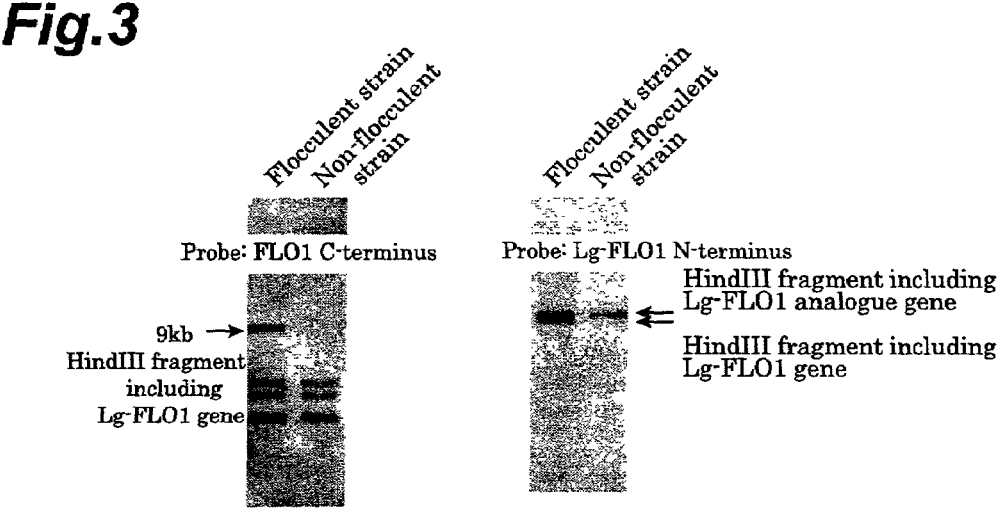
FIG. 3 is an autoradiogram showing the results of Southern analysis of the Lg-FLO1 analogue gene.

Upon Northern analysis, as shown in FIG. 2, a signal was also detected at a slightly lower molecular weight than that of the Lg-FLO1 gene for both the flocculent strains and the non-flocculent strains, when the Lg-FLO1 N-terminal portion was used as the probe. This gene was designated as the Lg-FLO1 analogue gene. When the FLO1 C-terminal portion was used as the probe, only the Lg-FLO1 gene was detected. Upon Southern analysis, as shown in FIG. 3, a signal was also detected at a somewhat higher molecular weight than the fragment including Lg-FLO1, for both the flocculent strains and the non-flocculent strains when the Lg-FLO1 N-terminal was used as the probe. Since this signal was not detected by Southern analysis using the FLO1 C-terminal portion as the probe, it was assumed to be the fragment containing the analogue gene.

The results to this point suggested that the ORF (Open Reading Frame) of the analogue gene has a slightly smaller molecular weight than Lg-FLO1 and has the same sequence as the Lg-FLO1 N-terminus, while its C-terminal portion differs from Lg-FLO1. In addition, data from Southern analysis not shown here confirmed that the analogue gene also has a site in common with Lg-FLO1 further upstream from the promoter region situated upstream from the N-terminal portion.

Figure 4:
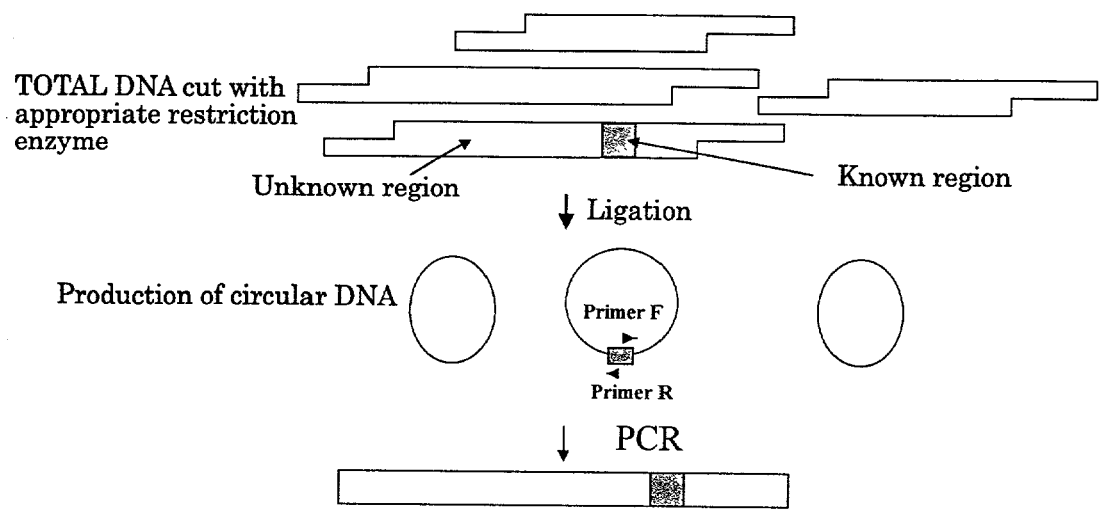
FIG. 4 is a schematic summary illustration of inverse PCR.

The total length of the analogue gene was obtained by inverse-PCR using the sequence-further upstream from the Lg-FLO1 promoter region as the primer. FIG. 4 shows a summary of the inverse-PCR procedure.

The two primers 5'-ACTAGAATTTAGGCACTTTCAAC-CCAGCCC-3' (SEQ. ID. No.15) and 5'-GCTGCAACCG-GAAGTTATTCCTTCTCCACT-3' (SEQ. ID. No.16) were synthesized based on the Lg-FLO1 promoter region base sequence reported by Kobayashi et al. (Japanese Patent Application Laid-Open Gazette No. HEI. 9-224676). A 20 μg amount of total DNA of the non-flocculent bottom-fermenting yeasts shown in Table 2 was digested with 300 units of restriction enzyme HindIII (Takara Shuzo Co., Ltd.), recovered by ethanol precipitation and then dissolved in 30 μL of TE buffer solution, after which a DNA ligation kit (Takara Shuzo Co., Ltd.) was used for self circular closure of the DNA fragments on a 30 μL scale. Nos. 1-16 in Table 2 correspond to the lane numbers in FIG. 8.

TABLE 2

| Name of strain (bottom-fermenting yeast) | Flocculating property evaluation | Name of strain (wild yeast) |
| --- | --- | --- |
| 1: NCYC965 | F0 | 11: Saccharomyces cerevisiae |
| 2: NCYC1324 | F0 | (ATCC 46967) |
| 3: W204 | F0 | 12: Saccharomyces |
| 4: W71 | F1 | diastaticus |
| 5: AJL3126 | F1 | 13: Pichia (IFO 0035) |
| 6: NCYC512 | F2 | 14: Saccharomyces bayanus |

TABLE 2-continued

| Name of strain (bottom-fermenting yeast) | Flocculating property evaluation | Name of strain (wild yeast) |
| --- | --- | --- |
| 7: NCYC719 | F2 | (IFO 0676) |
| 8: NCYC1250 | F2 | 15: Candida albicans |
| 9: VLB202 | F2 | (ATCC 10259) |
| 10: VLB He Bru | F2 | 16: Saccharomyces uvarum |
| | | (ATCC 44968) |

The expected result is formation of a circular molecule with the HindIII-digested sites linked, as shown in FIG. 4. The reaction product was recovered by ethanol precipitation, and approximately 10 μg thereof was used as a template for inverse-PCR with the aforementioned primers, using an LA-PCR kit (Takara Shuzo Co., Ltd.). The PCR conditions were 94° C. for 1 minute followed by 98° C. for 20 seconds and 68° C. for 10 minutes, repeated for 30 cycles. The obtained PCR product was subjected to electrophoresis using 1% agarose gel, and as a result the approximately 9.4 kb amplified fragment shown in FIG. 5 was observed. The PCR for the HindIII cleavage fragments containing the Lg-FLO1 genes from the flocculent strains was carried out according to the procedure of Kobayashi et al. (Japanese Patent Application Laid-Open Gazette No. HEI. 8-266287).

Figure 6:
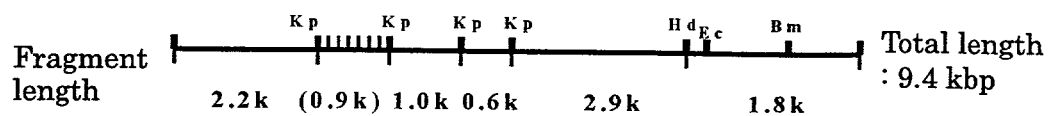
FIG. 6 is a schematic restriction enzyme map for the Lg-FLO1 analogue gene.

Next, a restriction enzyme map was prepared for the approximately 9.4 kb amplified fragment. The prepared restriction enzyme map is shown in FIG. 6. The 2.9 kb and 0.6 kb fragments cut with KpnI and HindIII were cloned using a Perfectly Blunt Cloning Kit (Novagen Co., Inc.), and used for base sequence determination. Also, a Kilosequence Deletion Kit (Takara Shuzo Co., Ltd.) was used to prepare deletion mutants according to the included protocol. The base sequence was determined with a DNA Sequencer (Applied Biosystems, Inc.) using a dRhodamine Terminator Cycle Sequence FS Ready Reaction Kit (Applied Biosystems, Inc.) Upon determining the partial base sequences at a total of six locations, all of the sequences matched for the most part with sequences further downstream than 21340 bp from the left telomere end of chromosome IX of Saccharomyces cerevisiae, i.e. 21340-21818 bp (SEQ. ID. No.1), 21743-22190 bp (SEQ. ID. No.2), 22353-22865 bp (SEQ. ID. No.3), 22926-23398 bp (SEQ. ID. No.4), 23944-24219 bp (SEQ. ID. No.5) and 24408-24997 bp (SEQ. ID. No.6). Each of these sequences differs in about 1-20 bases when compared with the base sequence of chromosome IX of Saccharomyces cerevisiae found in the data base, but the differences are believed to be due to genetic polymorphisms between the yeast strains or errors in determining the base sequences, and the genes are substantially identical.

Figure 7:
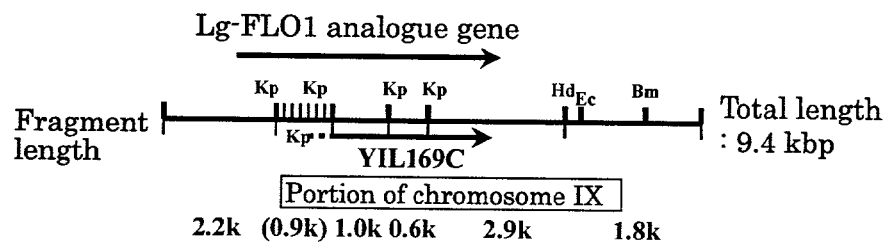
FIG. 7 is a schematic illustration showing the location of the YIL169c gene on the Lg-FLO1 analogue gene.

These results demonstrated that the Lg-FLO1 analogue gene is a fused gene of the Lg-FLO1 gene and a portion of chromosome IX of Saccharomyces cerevisiae. This portion of chromosome IX includes a gene designated as YIL169c (a gene analogous with the glucan 1,4-alpha-glucosidase gene and having an unknown function), and it is conjectured that most of the YIL169c gene is present at the C-terminal end of the analogue gene, as shown in FIG. 7.

Example 2

(Utilizing Lg-FLO1 Analogue Gene to Differentiate Bottom-Fermenting Yeast)

Figure 8:
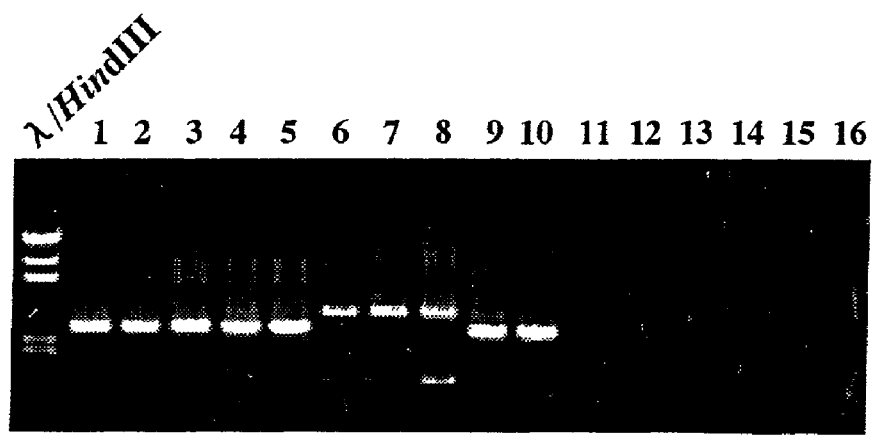
FIG. 8 is an electrophoresis photograph for differentiation between bottom-fermenting yeast and wild yeast using primers having the base sequences listed as SEQ. ID. Nos. 6 and 7.

A portion of the Lg-FLO1 analogue gene obtained in Example 1 was amplified by PCR for differentiation between bottom-fermenting yeast and wild yeast. The primers used for the PCR were sequences on the N-terminal portion of the Lg-FLO1 gene and a portion of the YIL169c gene included in the analogue gene. Specifically, the two primers 5'-GGAATACTGCCTCTTGGAGT-3' (SEQ. ID. No.7) and 5'-GGATTCTTCAGCGTTGAAGT-3' (SEQ. ID. No.8) were synthesized. These primers were used for PCR using the yeast total DNA as the template, in the same manner as Comparative Example 1. As shown in FIG. 8, this method allows differentiation even between bottom-fermenting yeast that has lost its flocculating property and wild yeast.

Example 3

The base sequence of the common portion of Lg-FLO1 and the aforementioned analogue gene was used for differentiation between bottom-fermenting yeasts and wild yeasts. The yeasts which were differentiated are shown in Table 3. Nos. 1-16 in Table 3 correspond to the lane numbers in FIG. 9.

TABLE 3

| Name of strain (bottom-fermenting yeast) | Flocculating property evaluation | Name of strain (wild yeast) |
|---|---|---|
| 1: NCYC965 | F0 | 11: *Saccharomyces cerevisiae* (ATCC 46967) |
| 2: NCYC1324 | F0 | 12: *Saccharomyces diastaticus* |
| 3: W204 | F0 | |
| 4: W71 | F1 | |
| 5: AJL3126 | F1 | 13: Pichia (IFO 0035) |
| 6: NCYC512 | F2 | 14: *Saccharomyces bayanus* (IFO 0676) |
| 7: NCYC719 | F2 | |
| 8: NCYC1250 | F2 | 15: *Candida albicans* (ATCC 10259) |
| 9: VLB202 | F2 | |
| 10: VLB He Bru | F2 | 16: *Saccharomyces uvarum* (ATCC 44968) |

Figure 9:
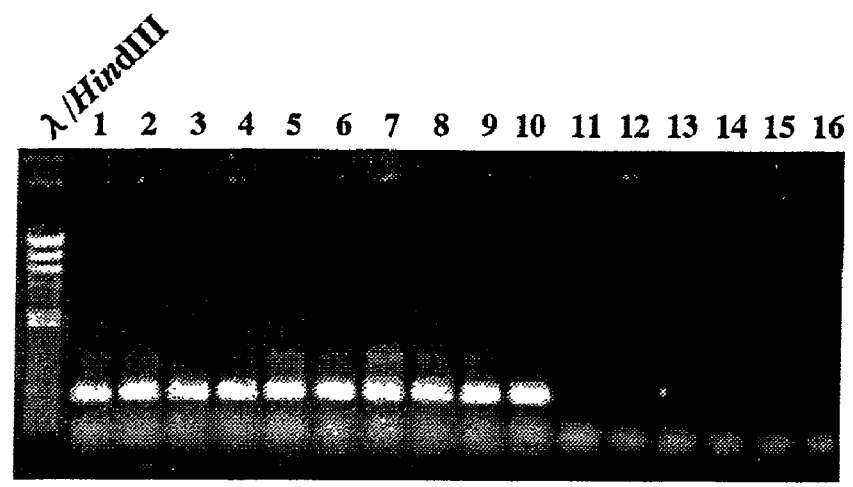
FIG. 9 is an electrophoresis photograph for differentiation between bottom-fermenting yeast and wild yeast using primers having the base sequences listed as SEQ. ID. Nos. 8 and 9.

The sequences 5'-AACGTAGCATCAGGAAGTACA-CAAGCATGC-3' (SEQ. ID. No.9) and 5'-GATCGGGTAAT-AGTAACCGGCGTACATGTA-3' (SEQ. ID. No.10) were synthesized as primers for PCR. This set of primers was used for PCR using the yeast total DNA as the template, in the same manner as Comparative Example 1. As shown in FIG. 9, it was possible to differentiate all of the bottom-fermenting yeasts from the wild yeasts in this case as well, regardless of the strength of the flocculating property.

As explained above, the method of differentiating bottom-fermenting yeast and wild yeast according to the invention provides a method of highly accurate differentiation between bottom-fermenting yeast and wild yeast.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method of differentiating bottom-fermenting yeast from wild yeast comprising synthesizing a pair of primers consisting of (i) a primer consisting of the base sequence set forth in SEQ ID NO: 7 and (ii) a primer consisting of 15-30 nucleotides of a sequence that is complementary to a base sequence of chromosome IX of *Saccharomyces cerevisiae* located downstream from a sequence selected from the group consisting of SEQ ID NO: 1, SEQ ID NO: 2, SEQ ID NO: 3, SEQ ID NO: 4, SEQ ID NO: 5, and SEQ ID NO: 6;

performing PCR (Polymerase Chain Reaction) to produce a PCR amplification product, wherein the primers for said PCR consist of said pair of primers, the template for said PCR is a DNA separated from a yeast specimen, and said PCR is performed by denaturing for 10 seconds to 2 minutes at a temperature of 90-98° C., annealing for 20 seconds to 2 minutes at a temperature of 40-75° C., and extending for 1-20 minutes at a temperature of 65-75° C., with 10-30 cycles; and differentiating whether said yeast is bottom-fermenting yeast or wild yeast, based on the PCR amplification product, wherein said wild yeast is yeast not used for brewing and said wild yeast belongs to a genus selected from the group consisting of the genus *Hansenula*, the genus *Brettanomyces*, the genus *Candida*, and the genus *Saccharomyces*, wherein when the wild yeast is from the genus *Saccharmyces* said wild yeast is a species selected from the group consisting of *Saccharomyces cerevisiae*, *Saccharomyces bayanus* and *Saccharomyces diastaticus*, and wherein said bottom-fermenting yeast is *Saccharomyces pastorianus*.

2. A method of differentiating bottom-fermenting yeast from wild yeast comprising synthesizing a pair of primers consisting of (i) a primer consisting of the base sequence set forth in SEQ ID NO: 7 and (ii) a primer consisting of the base sequence set forth in SEQ ID NO: 8;

performing PCR (Polymerase Chain Reaction) to produce a PCR amplification product, wherein the primers for said PCR consist of said pair of primers, the template for said PCR is a DNA separated from a yeast specimen, and said PCR is performed by denaturing for 10 seconds to 2 minutes at a temperature of 90-98° C., annealing for 20 seconds to 2 minutes at a temperature of 40-75° C., and extending for 1-20 minutes at a temperature of 65-75° C., with 10-30 cycles; and differentiating whether said yeast is bottom-fermenting yeast or wild yeast, based on the PCR amplification product, wherein said wild yeast is yeast not used for brewing and said wild yeast belongs to a genus selected from the group consisting of the genus *Hansenula*, the genus *Brettanomyces*, the genus *Candida*, and the genus *Saccharomyces*, wherein when the wild yeast is from the genus *Saccharmyces* said wild yeast is a species selected from the group consisting of *Saccharomyces cerevisiae*, *Saccharomyces bayanus* and *Saccharomyces diastaticus*, and wherein said bottom-fermenting yeast is *Saccharomyces pastorianus*.

3. A method of differentiating beer yeast comprising synthesizing a pair of primers consisting of (i) a primer consisting of the base sequence set forth in SEQ ID NO: 9 and (ii) a primer consisting of 15-30 bp of a sequence that is complementary to a base sequence of chromosome IX of *Saccharomyces cerevisiae* located downstream from a sequence selected from the group consisting of SEQ ID NO: 1, SEQ ID NO: 2, SEQ ID NO: 3, SEQ ID NO: 4, SEQ ID NO: 5, and SEQ ID NO: 6;

performing PCR (Polymerase Chain Reaction) to produce a PCR amplification product, wherein the primers for said PCR consist of said pair of primers, the template for said PCR is a DNA separated from a yeast specimen, and said PCR is performed by denaturing for 10 seconds to 2 minutes at a temperature of 90-98° C., annealing for 20 seconds to 2 minutes at a temperature of 40-75° C., and extending for 1-20 minutes at a temperature of 65-75° C., with 10-30 cycles; and differentiating whether said yeast is bottom-fermenting yeast or wild yeast, based on the PCR amplification product, wherein said wild yeast is yeast not used for brewing and said wild yeast belongs to a genus selected from the group consisting of the genus *Hansenula*, the genus *Brettanomyces*, the genus *Candida*, and the genus *Saccharomyces*, wherein when the wild yeast is from the genus *Saccharmyces* said wild yeast is a species selected from the group consisting of *Saccharomyces cerevisiae*, *Saccharomyces bayanus* and *Saccharomyces diastaticus*, and wherein said bottom-fermenting yeast is *Saccharomyces pastorianus*.

4. The method of differentiating beer yeast according to claim 3, wherein said pair of primers consists of (i) a primer comprising the base sequence set forth in SEQ ID NO: 9 and (ii) a primer comprising the base sequence set forth in SEQ ID NO: 10.

5. A pair of primers consisting of (i) a primer consisting of the base sequence set forth in SEQ ID NO: 7 and (ii) a primer consisting of the base sequence set forth in SEQ ID NO: 8.

6. A pair of primers consisting of (i) a primer comprising the base sequence set forth in SEQ ID NO: 9 and (ii) a primer comprising the base sequence set forth in SEQ ID NO: 10.

* * * * *

SEQUENCE LISTING

```
<160> NUMBER OF SEQ ID NOS: 16

<210> SEQ ID NO 1
<211> LENGTH: 479
<212> TYPE: DNA
<213> ORGANISM: Saccharomyces cerevisiae

<400> SEQUENCE: 1
agcttcaata aatgcgtgac tggctatagt tgtcggatgg caatccatta ttatgtatac      60
cgtattatta agagtgcaac taggcccgac tataaatcta acactcagat ccttgtactg     120
taatgcatat ttattttttc acaagttgca tgctaataat accatgatat ttttttttgaa    180 gccttgaaaa atagttcaag cagctacgat atcatgaatc aatatactca ttgcagccta    240
tgtaatatat ataggttccg tgttaccact cgtttctgat attttcgata tggctacact    300
gggtttttca tgatggaaat gtgatactac cagttccaat atatttatct tccttatcta    360
tatgacacgc tgttatttta gttcaagtca gtgtccaatt gaagtgagtg tcacgtgcac    420
agcgacggta gtcgttggat gtgctaaatg atgttctact gccaatgact gcaaatacg     479

<210> SEQ ID NO 2
<211> LENGTH: 448
<212> TYPE: DNA
<213> ORGANISM: Saccharomyces cerevisiae

<400> SEQUENCE: 2
gtgagtgtca cgtgcacagc gacggtagtc gttggatgtg ctaaatgatg ttctactgcc      60
aatgactgca aatacgttcg aagagtataa aatcgaagga aacgaattaa gttgccaatc    120
```

```
cttactgtaa ctatagcatg ttacatatat gtaccataag tatcacatta aggtttcgcc    180
atagccatgt gcctatatta aatagaaata tcacatggcg atccacggaa tgtttataga    240
ttttcttctt ttgtctatgg cccgggcgag acattaattt atcttgctga aaaattcgaa    300
agttaaaact caattatgcg tgggatttct caattaggtt accagaattt caatctgctg    360
aagaattatg tcttaaaaaa aaaaagtccc gcctcaaaaa agccaaaaag ggtgtgactg    420
tagattgtgg gtaacttgct gtcaaatg                                       448

<210> SEQ ID NO 3
<211> LENGTH: 513
<212> TYPE: DNA
<213> ORGANISM: Saccharomyces cerevisiae

<400> SEQUENCE: 3
tgtcggtaag atcttccgta gtggcaggtc aagcagtgag aagaaagat cggcagtaaa      60 ctgataagag ccaaaccgaa aagtttctta tacgcaaaaa cgctttgaaa attctccaag    120
aatcctattt gaaactctta ttaataaata agtataaat ataataaagt ttattgtgag    180
acatgtcgcg ataagcaccc cttgtctttc ttggaaggga gaaatttgta atataaagcc    240
aagtgctcag aactcgattt ttttctgacc aaagagcgga agctccacta taaaagttgg    300
gaggtacttt taggttctct taagttcgca tttaattatg gcctgaacga ttttactgtg    360
gacaataagt gaaataagtg tccttaaaat gtgtacgatg tgtacacatc aacctactct    420 cccttcatt ggcagaagag ggaaccattt catccaaaaa aaataaaaaa ataaaaaaaa    480
tccaaatatt aagctaaaaa aatacttaac tgt                                513

<210> SEQ ID NO 4
<211> LENGTH: 473
<212> TYPE: DNA
<213> ORGANISM: Saccharomyces cerevisiae

<400> SEQUENCE: 4
tttaattcct cagttaaaaa aattagttaa agaaagcaag aacgaaaata ccgaccaatg     60
cattcaaagt attggcattc aaacctgcgg caatacccct ggactggaca atgataccag    120
tagaggtctt tattggagct gcagatttgg agtatgtggg aaattgcact agaagccttg    180
gaaatggcag tagtcaatga ggttgcttta gaaccctcag aagtgacagt agtgtatgac    240
tttggagaag cactagttgc gtgacggttg aagtagcttc aggtatttta gaggtgatta    300
tcttgacgtt acaaccattg tcatcaccat tgagtaacca gtggcagtag tgtatgtcct    360
taggggcagc actggtttct gaagtttctg aagtttcttt aggagcttca gaagtgacag    420
tcttggtgct acatccattg tcatcgcact gagtaacagt agcggtggtg tat           473

<210> SEQ ID NO 5
<211> LENGTH: 276
<212> TYPE: DNA
<213> ORGANISM: Saccharomyces cerevisiae

<400> SEQUENCE: 5
aacggtttca gttacaacag caccggttga tgtactaacg tgacatccag tttcatcaca     60
agaagtaata gtggcggtag tggatgagca tggaacggtt gtggtaatgg tatagacgtt    120
accattggag tcagttgtct ctgaacaaga aactacgact gtgcttgtgg catttacata    180
gtctagtgtt gtagtgtaaa cagatgttga accggtaacg gaagcaccaa atgaagtgga    240
```

```
agcagttgaa ccggtaacgg aagcaccgaa tgaagt                                  276

<210> SEQ ID NO 6
<211> LENGTH: 590
<212> TYPE: DNA
<213> ORGANISM: Saccharomyces cerevisiae

<400> SEQUENCE: 6
caatagcaaa agagaattgt ctgttacctt gggttgcagt tagaacaccg gtagtaccgt         60
cataagaaag agcagtgatg tcagcggtaa tggcaatttg gttcttacca gtgtagccaa        120
caacaggaat aggagtggca ttggtttcgg ttgggtcaac agcaaggaca ccttcaccct        180
tgaatacaac agtttggcca gtaaatgtgt cagggtagtg taagtatagg ttaccggaaa        240
tgatgttgac tgtaccttt ccagaaactg gttcgacaat aacataggta cttccattgt         300
ctaggttaat ttcaccgttg tttactgaac cttcagtgtc gtctctacgt tgtagaccgg        360
aaacagaacc accgttgaga atagcgttcg agaaagagaa ggcaccagaa ttggagtatg        420
gagagaaagt gacttcaccc ttcttggact tgatagact taaggaaatg tcaccactgt        480
tgtcaaaaga acttggagtg aaggagtaga tggatgcaga ggtggcagcg gattcttcag        540
cgttgaagtt accggtcacg tcaaagtttt caccggagat gtcgaattcg                   590

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
ggaatactgc ctcttggagt                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
ggattcttca gcgttgaagt                                                    20

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9
aacgtagcat caggaagtac acaagcatgc                                         30

<210> SEQ ID NO 10
<211> LENGTH: 30
<212> TYPE: DNA
<213> ORGANISM: Artificial Sequence
<220> FEATURE:
<223> OTHER INFORMATION: Synthetic DNA

<400> SEQUENCE: 10
gatcgggtaa tagtaaccgg cgtacatgta                                         30
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
ggaatactgc ctcttggagt                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
ttaccatacg attgccagca                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
ttccaaccag tagttccacc                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
ggtcgcggaa gccgtctgtg                                          20

<210> SEQ ID NO 15
<211> LENGTH: 30
<212> TYPE: DNA
<213> ORGANISM: Artificial Sequence
<220> FEATURE:
<223> OTHER INFORMATION: Synthetic DNA

<400> SEQUENCE: 15
actagaattt aggcactttc aacccagccc                               30

<210> SEQ ID NO 16
<211> LENGTH: 30
<212> TYPE: DNA
<213> ORGANISM: Artificial Sequence
<220> FEATURE:
<223> OTHER INFORMATION: Synthetic DNA

<400> SEQUENCE: 16
gctgcaaccg gaagttattc cttctccact                               30
```